United States Patent
Nishizono et al.

(10) Patent No.: US 11,969,314 B2
(45) Date of Patent: Apr. 30, 2024

(54) METHOD AND APPARATUS FOR INCREASING SPERM MOTILITY

(71) Applicant: NICHIA CORPORATION, Anan (JP)

(72) Inventors: Hirofumi Nishizono, Jupiter, FL (US); Yasuo Fujikawa, Yokohama (JP); Tomohiro Tsurumoto, Yokohama (JP)

(73) Assignee: NICHIA CORPORATION, Anan (JP)

(*) Notice: Subject to any disclaimer, the term of this patent is extended or adjusted under 35 U.S.C. 154(b) by 413 days.

(21) Appl. No.: 16/825,047

(22) Filed: Mar. 20, 2020

(65) Prior Publication Data

US 2020/0297469 A1 Sep. 24, 2020

(30) Foreign Application Priority Data

Mar. 22, 2019 (JP) ................ 2019-055394

(51) Int. Cl.
*A61D 19/02* (2006.01)
*A61N 5/06* (2006.01)

(52) U.S. Cl.
CPC ............ *A61D 19/025* (2013.01); *A61N 5/06* (2013.01); *A61N 2005/0626* (2013.01); *A61N 2005/0651* (2013.01); *A61N 2005/0658* (2013.01)

(58) Field of Classification Search
CPC .............. A61D 19/025; A61N 5/06; A61N 2005/0626; A61N 2005/0651; A61N 2005/0658
See application file for complete search history.

(56) References Cited

U.S. PATENT DOCUMENTS

| | | |
|---|---|---|
| 5,453,354 A | 9/1995 | Akerlöf et al. |
| 5,780,230 A | 7/1998 | Li et al. |
| 6,379,939 B1 * | 4/2002 | Lubart ............... A61N 5/0613 435/2 |
| 2015/0328478 A1 | 11/2015 | McDaniel |
| 2017/0188573 A1 | 7/2017 | Codony Iglesias et al. |
| 2018/0125040 A1 | 5/2018 | Grajcar et al. |

FOREIGN PATENT DOCUMENTS

| | | |
|---|---|---|
| EP | 3 323 289 A1 | 5/2018 |
| JP | 2017-529085 A | 10/2017 |
| WO | WO-2015/056727 A1 | 4/2015 |
| WO | WO-2016/042384 A1 | 3/2016 |

OTHER PUBLICATIONS

Hoshi, Hiroyoshi, "Development and Commercialization of Serum-free Medium for In Vitro Fertilized Egg production", Research Division, Research Institute for the Functional Peptides Co., Ltd., pp. 1-6.

(Continued)

*Primary Examiner* — Gary Jackson
*Assistant Examiner* — Naveed R. Kolia
(74) *Attorney, Agent, or Firm* — Foley & Lardner LLP

(57) ABSTRACT

A method for treating spermatozoa of an animal includes: irradiating the spermatozoa with light having wavelengths in a range of 390-420 nm at a fluence effective to increase motility of the spermatozoa by 75% or more.

20 Claims, 4 Drawing Sheets

(56) References Cited

OTHER PUBLICATIONS

Nagata, Maria Portia B. et al., "Live births from artificial insemination of microfluidic-sorted bovine spermatozoa characterized by trajectories correlated with fertility", PNAS, Mar. 19, 2018, pp. E3087-E3096, vol. 115, No. 14.
Ankri et al.—"Visible Light Induces Nitric Oxide (NO) Formation in Sperm and Endothelial Cells"; 2010; Lasers in Surgery and Medicine; p. 42: 348-352.
Corral-Basques et al.—"The Effect of low-level laser irradiation on dog spermatozoa motility is dependent on laser output power"; Sep. 12, 2008; Laser Med Sci; p. 24:703-713.
Frangez et al.—"Photobiomodulation with light-emitting diodes improves sperm motility in men with asthenozoospermia"; Sep. 10, 2014; Lasers Med Sci; p. 30:235-240.
Lavi et al.—"Detailed Analysis of Reactive Oxygen Species Induced by Visible Light in Various Cell Types"; 2010; Lasers in Surgery and Medicine; p. 42:473-480.
Shahar et al.—"Light-mediated activation reveals a key role for protein kinase A and sarcoma protein kinase in the development of sperm hyper-activated motility"; Jul. 19, 2011; Human Reproduction; vol. 26, No. 9, p. 2274-2282.
Yeste et al.—"Impact of light irradiation on preservation and function of mammalian spermatozoa"; Feb. 9, 2018; Elsevier; Animal Reproduction Science 194; p. 19-32.
Zan-Bar et al.—"Influence of Visible Light and Ultraviolet Irradiation on Motility and Fertility of Mammalian and Fish Sperm"; 2005; Photomedicine and Laswer Surgery; vol. 23, No. 6; p. 549-555.
Fujiwara, A. et al., Activating Effect of Light Irradiation at Various Wavelength on the Respiration in Sperm of the Echiuroid, *Urechis unicinctus*, in the Presence of Carbon Monoxide, The Journal of Biochemistry, 1991, vol. 109, Issue 3, pp. 486-491.

\* cited by examiner

METHOD AND APPARATUS FOR INCREASING SPERM MOTILITY

CROSS-REFERENCE TO RELATED APPLICATION

This application claims priority under 35 USC § 119 to Japanese Patent Application No. 2019-055394, filed on Mar. 22, 2019, the contents of which are incorporated herein by reference in their entirety.

TECHNICAL FIELD

The present disclosure relates to a method and apparatus for increasing sperm motility. More particularly, the disclosure relates to a method and apparatus for increasing the motility of animal spermatozoa by means of irradiation with light in specified wavelengths.

BACKGROUND

Various animals including livestock are bred by artificial insemination. However, in cattle for example, the conception rate in artificial insemination has been decreasing in recent years. Thus, there are needs to develop techniques for improving the conception rate, and various studies therefor have been and are being conducted.

For example, a technique has been developed for improving the conception rate by culturing fertilized eggs in vitro in a specific medium (WO 2015/056727).

As for spermatozoa, it is known that the use of highly motile ones results in high conception rate, and therefore, studies focusing on sperm motility have been and are being conducted. For example, techniques have been developed for activating sperm motility by chemical agents (U.S. Pat. Nos. 5,453,354 and 5,780,230). Nagata MPB et al. (PNAS, 2018, 115(14), E3087-3096) reports a sperm sorting system for the selection and separation of motile sperm. However, the use of chemicals raises safety concerns and complicated techniques are time-consuming and costly. It has been reported that the addition of a chemical substance to a medium for spermatozoa or fertilized eggs may adversely affect conception, especially in cattle (H. Hoshi, Development and Commercialization of Serum-free Medium for In Vitro Fertilized Egg Production (Research Division, Functional Peptide Research Institute, Inc.).

Simple techniques have also been developed for increasing sperm motility by light irradiation. U.S. Pat. No. 6,379,939 discloses a method for improving sperm motility by irradiating the spermatozoa with light in the extended visible range. Japanese Patent Publication No. 2017-529085 (equivalent to WO 2016/042384) discloses a method for increasing sperm motility by irradiating with red light (having a wavelength between 620-630 nm) in a discontinuous manner.

U.S. Pat. No. 6,379,939 states that the method increased the sperm motility by about 50%. The patent document does not disclose or suggest that light in a certain wavelength range can efficiently increase the motility.

Japanese Patent Publication No. JP 2017-529085 states that the method significantly improved the sperm motility, but does not specifically indicate the degree of the increase. The publication does not disclose or suggest that light in a specific range other than the red light range used can efficiently increase the motility.

There remains a need for methods and apparatuses for more efficiently increasing the motility of animal spermatozoa.

SUMMARY

The present disclosure provides a method for treating spermatozoa of an animal, comprising irradiating the spermatozoa with light having wavelengths in a range of 390-420 nm at a fluence effective to increase the motility of the spermatozoa by 75% or more.

The present disclosure also provides a method for preparing spermatozoa having increased motility, comprising treating spermatozoa of an animal with the above-mentioned method.

The present disclosure also provides an apparatus for treating spermatozoa of an animal to increase the motility, comprising: a holding or mounting unit configured to hold or support a sperm container; a lighting unit configured to be able to irradiate the sperm container held or supported by the holding or mounting unit with light having wavelengths in a range of 390-420 nm; and a light controller unit configured to control the lighting unit.

DETAILED DESCRIPTION

Figure 1A:
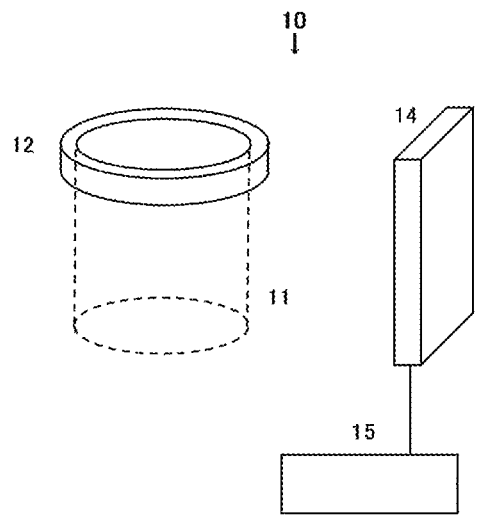
FIG. 1A illustrates a sperm treatment apparatus according to a first embodiment of the present invention.
Figure 1B:
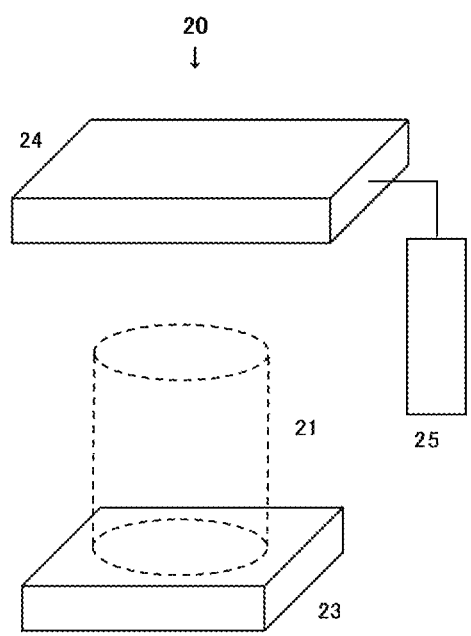
FIG. 1B illustrates a sperm treatment apparatus according to a second embodiment of the invention.
Figure 1C:
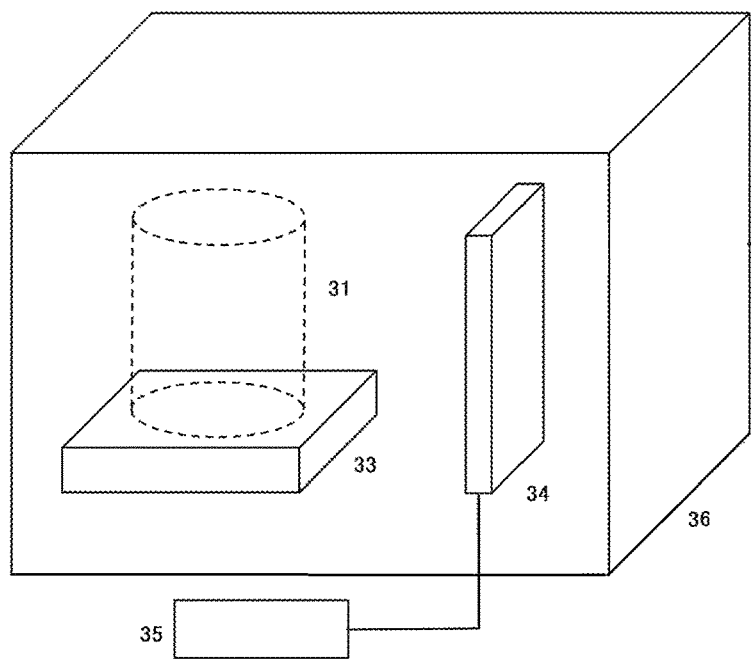
FIG. 1C illustrates a sperm treatment apparatus according to a third embodiment of the invention.
Figure 1D:
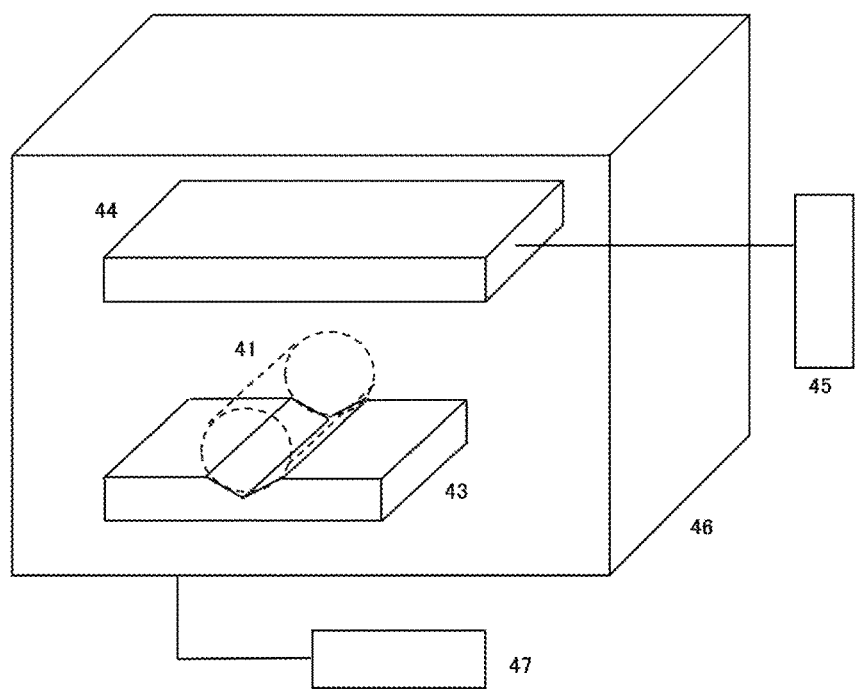
FIG. 1D illustrates a sperm treatment apparatus according to a fourth embodiment of the invention.

Unless defined otherwise, all technical and scientific terms used herein have the same meaning as is commonly understood by one of ordinary skill in the art to which the disclosure belongs. Although any apparatuses, devices, methods, and materials similar or equivalent to those described herein can be used in the practice or testing of the disclosure, representative apparatuses, devices, methods, and materials are now described.

As used herein and in the appended claims, the singular forms "a", "an" and "the" include plural referents unless the context clearly dictates otherwise. The terms "comprise", "comprising", "include," "including," "have," "has," "having," and the like are intended to be inclusive and mean that there may be additional elements other than the listed elements.

As used herein and in the appended claims, a numerical range "a to b" or "a-b" ("a" and "b" represent specific numerical values) means the range including both of the values "a" and "b", that is, the range "between a and b (both inclusive)".

Sperm Treatment Method

In one aspect, a method for treating spermatozoa (or sperm cells) of an animal, particularly to improve their motility, is provided.

A method for treating animal spermatozoa according to the disclosure (also referred herein to as "present treatment method") includes irradiating the animal spermatozoa with light having wavelengths in a range of 390-420 nm at a fluence effective to increase the motility of the spermatozoa by 75% or more.

The disclosure is based on the findings that irradiating animal spermatozoa with light having wavelengths in a range of 390-420 nm can increase their motility more significantly compared with the irradiation with light in other wavelengths, as shown in the Examples below. Thus, according to a method of the disclosure, the sperm motility can be increased efficiently.

In the present specification, the "motility" can be evaluated on the basis of at least one parameter selected from the group consisting of the percentage of motile spermatozoa, active sperm concentration, straight-line velocity (VSL), curvilinear velocity (VCL), average path velocity (VAP), amplitude of lateral head displacement (ALH) and beat-cross frequency (BCF). The parameters can be measured using a computer-assisted sperm analyzing system (CASA), for example. An example of CASA includes a Sperm Motility Analysis System (SMAS). Preferably, the motility can be evaluated on the basis of at least one parameter selected from the group consisting of straight-line velocity, curvilinear velocity, average path velocity, amplitude of lateral head displacement and beat-cross frequency, and more preferably straight-line velocity, curvilinear velocity and average path velocity. In some embodiments, the motility is evaluated on the basis of average path velocity (VAP). For evaluation, a mean value of the measurements in a plurality of different fields (three different fields, for example) can be used.

In the present disclosure, the spermatozoa (or sperm cells) are irradiated with light having a wavelength range effective to increase their motility (also referred herein to as light in "the specified wavelengths"), specifically having wavelengths in a range of 390-420 nm, more specifically 395-415 nm, and more specifically 400-410 nm.

The fluence (or dose) of the light in the specified wavelengths irradiated to the spermatozoa is not limited so long as it is an amount effective to increase the sperm motility by 75% or more. The fluence is preferably an amount effective to increase the motility by 90% or more, more preferably by 100% or more, more preferably by 125% or more, more preferably by 150% or more, and more preferably by 175% or more. The specific fluence may vary according to the kind of animal from which the spermatozoa used are derived. For bovine spermatozoa, the specific fluence may be, for example, in a range of 450-7000 mJ/cm$^2$, 450-6500 mJ/cm$^2$, preferably 450-6000 mJ/cm$^2$, more preferably 500-6000 mJ/cm$^2$, more preferably 500-5500 mJ/cm$^2$, more preferably 500-5000 mJ/cm$^2$, more preferably 500-4500 mJ/cm$^2$, more preferably 550-4500 mJ/cm$^2$, more preferably 550-4000 mJ/cm$^2$, more preferably 550-3500 mJ/cm$^2$, more preferably 550-3000 mJ/cm$^2$, more preferably 600-3000 mJ/cm$^2$, more preferably 600-2500 mJ/cm$^2$, more preferably 600-2000 mJ/cm$^2$, more preferably 600-1500 mJ/cm$^2$, more preferably 650-1500 mJ/cm$^2$, and more preferably 650-1000 mJ/cm$^2$.

In the present treatment method, the "fluence" may be measured at the light-receiving surface of a semen sample or a suspension of spermatozoa. For example, the fluence may be measured at an area on the outer surface of a container containing the sample or suspension, which area corresponds to the light-receiving surface of the sample or suspension.

The irradiance (or fluence rate) of the light in the specified wavelengths irradiated to the spermatozoa is not limited so long as it is an amount effective to increase the motility of the irradiated spermatozoa by a predefined value as described above, and may be, for example, in a range of 0.1-200 mW/cm$^2$, preferably 0.1-150 mW/cm$^2$, more preferably 0.1-100 mW/cm$^2$, more preferably 0.1-50 mW/cm$^2$, more preferably 0.1-20 mW/cm$^2$, more preferably 0.1-10 mW/cm$^2$, more preferably 0.1-5 mW/cm$^2$, more preferably 0.1-2 mW/cm$^2$, more preferably 0.1-1 mW/cm$^2$, more preferably 0.1-0.8 mW/m$^2$, and more preferably 0.1-0.5 mW/m$^2$. Irradiation at an irradiance of less than 0.1 mW/cm$^2$ or more than 200 mW/cm$^2$ may not efficiently improve the sperm motility. In the present treatment method, the "irradiance" is an amount at the light-receiving surface of a semen sample or a suspension of spermatozoa. For the irradiance, an amount may be substituted, which is measured at an area on the outer surface of a container containing the sample or suspension, which area corresponds to the light-receiving surface of the sample or suspension.

The irradiation time of the light in the specified wavelengths is not particularly limited so long as it is an amount effective to increase the motility of the irradiated spermatozoa by a predefined value as described above, and may be, for example, in a range of 1-90 min, preferably 1-60 min, more preferably 2-60 min, more preferably 5-60 min, more preferably 5-30 min, and more preferably 10-30 min. The irradiation at a time of less than 1 min or more than 90 min may not efficiently improve the sperm motility.

The light in the specified wavelengths may be irradiated as continuous light or intermittent light (such as pulsed light). The use of intermittent light can avoid or reduce a rise in temperature of the spermatozoa irradiated and/or the light source of the light in the specified wavelengths. The pulse width of the pulsed light may be, for example, 100 ms or less, more particularly 50 ms or less, more particularly 20 ms or less, more particularly 10 ms or less, and more particularly 5 ms or less. The duty ratio of the pulsed light may be, for example, 50% or less, more particularly 40% or less, more particularly 30% or less, more particularly 20% or less, more particularly 10% or less, and more particularly 5% or less.

The light in the specified wavelengths may be emitted by a single light source, or may be a mixed or composite light emitted by two or more light sources. If the light in the specified wavelengths is combined with light in other wavelengths, they may be irradiated simultaneously (as a mixed or composite light) or alternately. Examples of the light combined with the light in the specified wavelengths include light having wavelengths in a range of 615-635 nm. The irradiation of spermatozoa with the light having wavelengths in a range of 615-635 nm can increase their motility significantly, but the amount of the increase is much less than that obtained by the irradiation with the light in the specified wavelengths, as shown in the Examples below. Thus, the irradiation with a combination of the light in the specified wavelengths and the light having wavelengths in a range of 615-635 nm may increase the sperm motility more efficiently than the irradiation with the light in the specified wavelengths alone.

Where the light in the specified wavelengths is combined with light in other wavelengths to irradiate to the spermatozoa with a mixed or composite light, it is preferable that the irradiance of the light in the specified wavelengths is higher than that of the light in other wavelengths. Thus, in some preferred embodiments, the irradiance of the light having wavelengths in a range of 390-420 nm is 50% or more, more preferably 60% or more, more preferably 70% or more, more preferably 80% or more, more preferably 90% or more, more preferably 95% or more, and more preferably 100%, of the total irradiance of the light (i.e., the irradiance of the light in the entire wavelength range) irradiated to the spermatozoa. The embodiments can improve energy intensiveness, and increase the sperm motility more efficiently.

Preferably, the light in the specified wavelengths has a maximum peak wavelength in the range of 390-420 nm, more preferably 395-415 nm, and more preferably 400-410 nm. Use of such light is preferable in that the spermatozoa can be efficiently irradiated with the light in the specified wavelengths, which light can efficiently increase the motility of spermatozoa.

Accordingly, in some embodiments, the light in the specified wavelengths has a wavelength spectrum with a peak wavelength at 405±15 nm (and more preferably at 405±10 nm) and a half-width of 0.1-50 nm (and more preferably 0.1-20 nm). The embodiments can improve energy intensiveness, and increase the sperm motility more efficiently.

The light in the specified wavelengths may be a light component extracted by means of an optical filter from light emitted by a light source, such as halogen lamp, having a broad emission spectrum.

The light in the specified wavelengths may include, or consist of, light emitted by a light-emitting diode (LED) or laser diode (LD). In view of energy efficiency and economic efficiency, use of LED or LD is preferable due to the energy intensiveness, low heat generation, low power consumption and long life. In addition, the fluence can be easily controlled.

In the present specification, an animal is for example a vertebrate, which may be selected from mammals, birds and fishes, more preferably from mammals and birds, and more preferably from mammals. The animal may be a human and/or a non-human animal. The non-human animals include industrial animals (e.g., farm animals), race horses, pet or companion animals, zoo animals and endangered animals. Specific examples of mammals include humans, non-human primates, cattle (or bulls), horses, pigs, sheep, goats, rabbits, dogs and cats. Specific examples of birds include chickens, ducks, dabbling ducks, turkeys, guinea fowls, gooses and ostriches. Specific examples of fishes include salmons, trouts, sturgeons, tunas, goldfishes, nishikigoi (or colored carp), zebrafishes and medaka (or Japanese rice fishes).

The spermatozoa may be those at any point in time between collection and insemination, for example, a time point between collection and loading in a sperm container (such as straw), during thawing, or after thawing and before insemination.

During the irradiation, the spermatozoa are placed in such a container that does not block the irradiation of the spermatozoa in the inside with light including the light at the specified wavelengths. The container may be, for example, a petri dish, a beaker, a test tube, a microtube, a straw tube, or the like. The materials of the container are not particularly limited. Preferably, at least a portion of the container is made of a material transparent to light (in particular, the light in the specified wavelengths) irradiated to the spermatozoa according to the present treatment method, so that the light can transmit from the outside to the inside of the container.

During the irradiation, the concentration of spermatozoa is not particularly limited, and may be, for example, in a range of 100,000/mL to 10,00,000/mL, more specifically 500,000/mL to 10,00,000/mL, more specifically 1,000,000/mL to 10,00,000/mL, and more specifically 3,000,000/mL to 6,000,000/mL.

During the irradiation, the spermatozoa may be present in a buffered physiological solution, a sperm preincubation medium, or a sperm storage medium. The medium may be any of the commonly-used mediums for animal spermatozoa. Examples of media include, but not limited to, TCM-199 medium, BO medium, CR1 medium, SOF medium, NCSU medium, PZM-5 medium, HTF medium, TALP medium, BWW medium, TYH medium, DMEM medium, Ham-F10 medium, Whitten medium, Whittingham medium, M16 medium, and a modifications thereof. The medium may contain any of the commonly-used additive, as required. The additives include agents for improving sperm viability and inducers of sperm capacitation. Examples of additives include, but are not limited to, serum (such as fetal calf serum), serum albumin (such as human serum albumin and bovine serum albumin), pyruvate, calcium, cyclodextrin and derivatives thereof. The medium for cryopreservation may further contain hen's egg yolk, glycerin (or glycerol), ethylene glycol and/or dimethyl sulfoxide (DMSO), for example.

The spermatozoa may be agitated during the irradiation. The agitation can be carried out using a shaker or a stirrer.

During the irradiation, the spermatozoa are heated to and/or kept at a temperature near the body temperature of the animal from which the spermatozoa are derived (for animals other than fish), or the water temperature in the spawning season of the fish from which the spermatozoa are derived. The body temperature of the animal (except fish) may vary according to the kind of animal and may be, for example, in a range of 35 to 45° C. The water temperature for fish spawning may vary according to the kind of fish and may be, for example, in a range of 15 to 30° C.

The spermatozoa treated with the present treatment method can be used for artificial insemination, in-vitro insemination, and/or micro-insemination. The spermatozoa treated with the present treatment method may be cryopreserved until used for artificial insemination, in-vitro insemination, and/or micro-insemination.

Sperm Preparation Method

In another aspect, a method for preparing animal spermatozoa having increased motility is provided.

A method for preparing spermatozoa having increased motility according to the disclosure (also referred herein to as "present preparation method") includes treating spermatozoa of an animal with a treatment method described in the <Sperm treatment method> section above.

The present preparation method can prepare spermatozoa having an increased motility (and therefore increased fertilizing ability) efficiently in terms of time and/or cost, for example.

The spermatozoa prepared by the present preparation method (a preparation of spermatozoa) can be used for artificial insemination, in-vitro insemination, and/or micro-insemination. The preparation of spermatozoa may be cryopreserved until used for artificial insemination, in-vitro insemination, and/or micro-insemination.

The animals in the context of the present preparation method are as described in the <Sperm treatment method> section above.

The spermatozoa used in the present preparation method may be non-cryopreserved, cryopreserved or thawed spermatozoa. Cryopreserved spermatozoa can be used in the present preparation method during and/or after thawing.

In the present preparation method, spermatozoa may be loaded in a suitable transport or storage container before or after the treatment with a present treatment method. Thus, in some embodiments, the present preparation method further includes loading the spermatozoa in a suitable transport or storage container before or after treating the spermatozoa with a present treatment method. The transport or storage container may be a petri dish, a beaker, a test tube, a microtube, a straw tube, or the like.

In the present preparation method, the spermatozoa may be frozen after the treatment or the loading. Thus, in some embodiments, the present preparation method further includes freezing the spermatozoa after the treatment or the loading.

Sperm Treatment Apparatus

In still another aspect, an apparatus for treating spermatozoa (or sperm cells) of an animal to increase their motility is provided.

An apparatus for treating animal spermatozoa according to the disclosure (also referred herein to as "present treatment apparatus") includes: a holding or mounting unit configured to hold or support a sperm container; a lighting unit configured to be able to irradiate the sperm container held or supported by the holding or mounting unit with light having wavelengths in a range of 390-420 nm; and a light controller unit configured to control the lighting unit.

The present treatment apparatus is suitable for carrying out the present treatment method as described above.

In the context of the present treatment apparatus, the "animal" is a human and/or a non-human animal as described in the <Sperm treatment method>section above.

Embodiments of the treatment apparatus will be now described with reference to FIGS. 1A to 1D.

In some embodiments (FIGS. 1A and 1D), the treatment apparatus 10 includes a holding unit 12 configured to hold a sperm container 11 (indicated by the dashed line in the figure), a lighting unit 14 configured to be able to irradiate the container 11 held by the holding unit with light having wavelengths in a range of 390-420 nm, and a light controller unit 15 configured to control the lighting unit.

In other embodiments (FIGS. 1B to 1D), the treatment apparatus 20, 30, 40 includes a mounting unit 23, 33, 43 configured to support a sperm container 21, 31, 41 (indicated by the dashed line in the figures), a lighting unit 24, 34, 44 configured to be able to irradiate the container 21, 31, 41 supported by the mounting unit with light having wavelengths in a range of 390-420 nm, and a light controller unit 25, 35, 45 configured to control the lighting unit.

The present treatment apparatus includes at least one holding unit 12 or at least one mounting unit 23, 33, 43, which is configured to hold or support a sperm container 11, 21, 31, 41. The holding unit or mounting unit can be designed appropriately according to the sperm container used. The sperm container 11, 21, 31, 41 used with the present treatment apparatus may be, for example, a petri dish, a dish, a beaker, a sample cup, a test tube, a microtube, a straw tube, or the like.

The holding unit 12 is configured to hold the container 11 in a detachable manner. The holding unit is not particularly limited so long as it has a structure configured to hold and a size sufficient to hold the sperm container used, in a predefined position or area. The holding unit is not limited to one for holding the sperm container in an upright or standing position, and may be one for holding the container in a tilted, lying or inverted position, provided that the spermatozoa in the inside do not leak out.

The holding unit may be configured to receive at least a portion of the sperm container therein. In this case, the holding unit has, for example, a hollow cylindrical body member to hold the sperm container by receiving the bottom or the bottom and the side wall in the hollow.

The holding unit may hold the sperm container by supporting at least a portion thereof. The portion to be supported (at a point, line or surface) may be any portion of the container, and may be, for example, a bottom, side or top portion, or any combination thereof.

In some embodiments, the holding unit has a set of two or more pinching or gripping arm members, one arm member of which is movable and which are arranged to simultaneously contact the side surface of the sperm container, so that the holding unit holds the container by pinching or gripping with the arm members.

In other embodiments, the holding unit has one or more grooves, each having a rectangular, triangle, or arc cross section, so that the holding unit holds the sperm container in the groove with contacting and supporting the side surface of the container (for example, straw tube's outer circumferential surface) on the side wall.

In other embodiments, the holding unit has a first holding member to support one end of the sperm container, and a second holding member to support the other end of the container and/or a third holding member to support a middle portion of the container. The holding members may be designed appropriately according to the shape of the container used. For example, the first holding member may be a plate structure, by which the bottom of the container is supported on the top surface when the holding unit holds the container. The second and third holding members may each have an opening and support the side surface of the container in the opening.

The holding unit may be made of, for example, metal (such as stainless steel or brass), glass or plastic (such as acrylic resin, polycarbonate resin or polyvinyl chloride resin). If at least a portion of the holding unit may be positioned on the optical path of light emitted from the lighting unit to the sperm container, the portion is preferably made of a material transparent to the light (including the light in the specified wavelengths).

The mounting unit 23, 33, 43 is not particularly limited so long as it has a structure capable of mounting and a size sufficient to mount the sperm container used 21, 31, 41 on the top surface. The mounting unit is not limited to one for supporting the sperm container in an upright or standing position and may be one for supporting the container in a lying or inverted position, provided that the spermatozoa in the inside do not leak out.

The mounting unit may be composed of, for example, at least a portion of the top surface of a shelf or table, the inner bottom surface of a box, tray or basket, or the inner bottom surface of a housing. The mounting surface is not limited to a continuous surface, and may be composed of a plurality of discrete surfaces, or may be an imaginary surface such as the top surface of a mesh or grid shelf. The mounting unit may be made of, for example, metal (such as iron, stainless steel, aluminium or brass), glass or plastic (such as acrylic resin, polycarbonate resin or polyvinyl chloride resin). In the embodiments wherein the light from the lighting unit is transmitted through the mounting unit to the sperm container mounted or placed on the mounting surface, at least a portion of the mounting unit is preferably made of a material transparent to the light (including the light in the specified wavelengths).

The mounting unit may have a recess or a protrusion(s) defining an area (mounting surface) where the sperm container is mounted or placed, or an area irradiated with the light from the lighting unit. If the mounting unit has a recess, the sperm container may be mounted or placed on the bottom of the recess. If the mounting unit has a protrusion or plural protrusions, the sperm container may be mounted or placed on the top surface of the protrusion or in the area defined by the protrusions.

The top-view shape of the mounting surface may be, for example, circular or rectangular.

The mounting unit may have an anti-slipping member or a stopper member. If the mounting unit has an anti-slipping member, the mounting surface may be composed of the top surface of the anti-slipping member. The anti-slipping member may be made of a material capable of producing a large friction force by contacting with a portion of the sperm container.

The holding or mounting unit may be provided with a rotating or shaking mechanism to rotate or shake the sperm container. The shaking mechanism may be a rotary or reciprocal shaking mechanism. The rotating or shaking mechanism can easily provide more homogeneous irradiation of the spermatozoa in the sperm container with the light in the specified wavelengths. The shaking mechanism may allow the agitation of the spermatozoa in a buffered physiological solution, a sperm preincubation medium, or a sperm storage medium, while irradiating them with the light in the specified wavelengths. In specific embodiments, the mounting unit is composed of a turntable.

The present treatment apparatus 10, 20, 30, 40 includes at least one lighting unit 14, 24, 34, 44. The lighting unit is arranged to allow the irradiation of the container 11, 21, 31, 41 (and therefore, the spermatozoa contained in the container when used), which is held by the holding unit 12 or mounted on the mounting unit 23, 33, 43, with the light (including the light in the specified wavelengths) emitted from the lighting unit. The lighting unit may be situated so that the emitted light can be irradiated to the sperm container in at least one direction of a downward direction (from the overhead of the container, for example), an upward direction (from beneath the container, for example) and a lateral direction (from right beside the container, for example).

The lighting unit includes at least one light source configured to emit at least the light in the specified wavelengths, that is, the light having wavelengths in a range of 390-420 nm, more particularly 395-415 nm, and more particularly 400-410 nm. Examples of such a light source include light-emitting devices (LEDs), laser diodes (LDs), sodium lamps, xenon lamps, fluorescent lamps, incandescent lamps, white lamps, metal hydride lamps, high-pressure sodium lamps, and the like. If the percentage in radiance of the light in the specified wavelengths in the light emitted by the light source used is relatively low (for example, less than 50%, more particularly less than 40%, and more particularly less than 30%), it is preferable that a filter is used to increase the percentage, which filter has a higher transmittance in the specified wavelengths than in the other wavelengths.

In view of energy efficiency, the light source configured to emit the light in the specified wavelengths preferably is a light source configured to mainly emit the light having wavelengths in a range of 390-420 nm, and more preferably a light source configured to substantially exclusively emit the light having wavelengths in a range of 390-420 nm.

In the present specification, the phrase "light source configured to mainly emit the light having wavelengths in a range of 390-420 nm" refers to a light source configured to emit the light having wavelengths in a range of 390-420 nm at an irradiance that is 50% or more of, more particularly 55% or more of, more particularly 60% or more of, more particularly 65% or more of, more particularly 70% or more of, more particularly 75% or more of, more particularly 80% or more of, more particularly 85% or more of, and more particularly 90% or more of the total irradiance of the light emitted by the light source (i.e., the irradiance of the light in the entire wavelength range). In the present specification, the phrase "light source configured to substantially exclusively emit the light having wavelengths in a range of 390-420 nm" refers to a light source configured to emit the light having wavelengths in a range of 390-420 nm at an irradiance that is 95% or more of, more particularly 98% or more of, and more particularly 99% or more of the total irradiance of the light emitted by the light source.

The light source configured to mainly or substantially exclusively emit the light having wavelengths in a range of 390-420 nm may be a light source configured to emit light having the maximum peak wavelength in the range of 390-420 nm, preferably 395-415 nm, and more preferably 400-410 nm. More specifically, such a light source may be configured to emit light having a wavelength spectrum with a peak wavelength at 405±15 nm (and preferably at 405±10 nm) and a half-width of 0.1-50 nm (and preferably 0.1-20 nm), and more preferably the light source may have a single peak in the emission spectrum. Examples of such light sources include light-emitting devices (LEDs) and laser diodes (LDs). The light source may be a cluster or an array of LEDs or LDs. In view of energy efficiency and economic efficiency, use of LED or LD is preferable due to the energy intensiveness, low heat generation, low power consumption and long life. In addition, the fluence or the irradiance (fluence rate) can be easily controlled.

The lighting unit may include a light source configured to mainly or substantially exclusively emit the light having wavelengths in a range of 390-420 nm and a light source configured to emit light in the other wavelengths. The light source configured to emit the light in the other wavelengths may be a light source configured to emit light having wavelengths in a range of 615-635 nm.

The light source may have any configuration and can be designed appropriately according to the shape of the sperm container used, the arrangement of the light source and the container, and/or others. Specific examples of the light source may include a line light source and a panel light source.

The present treatment apparatus 10, 20, 30, 40 includes a light controller unit 15, 25, 35, 45 configured to control the lighting unit 14, 24, 34, 44.

The light controller unit may be configured to control the lighting unit to emit continuous light or intermittent light or a combination thereof. The use of intermittent light can avoid or reduce a rise in temperature of the spermatozoa irradiated and/or the light source.

The light controller unit may be configured to control the lighting unit to emit pulsed light whose pulse width is, for example, 100 ms or less, more particularly 50 ms or less, more particularly 20 ms or less, more particularly 10 ms or less, and more particularly 5 ms or less, and whose duty ratio is, for example, 50% or less, more particularly 40% or less, more particularly 30% or less, more particularly 20% or less, more particularly 10% or less, and more particularly 5% or less.

The light controller unit may be configured to control the lighting unit to emit light in such a manner that the irradiance of the light in the specified wavelengths is in the predefined range. In the context of the present treatment apparatus, the "irradiance" is an amount that is measured at an area on the inner or outer surface (preferably the outer surface) of the sperm container.

The predefined range may vary according to the kind of animal, from which the spermatozoa used are derived. The predefined range may be, for example, in a range of 0.1-200 mW/cm$^2$, preferably 0.1-150 mW/cm$^2$, more preferably 0.1-100 mW/cm$^2$, more preferably 0.1-50 mW/cm$^2$, more preferably 0.1-20 mW/cm$^2$, more preferably 0.1-10 mW/cm$^2$, more preferably 0.1-5 mW/cm$^2$, more preferably 0.1-2 mW/cm$^2$, more preferably 0.1-1 mW/cm$^2$, more preferably 0.1-0.8 mW/m$^2$, and more preferably 0.1-0.5 mW/m$^2$. Controlling the light source of the lighting unit in such a manner as described above can provide the spermatozoa in the container with the irradiation at an irradiance or fluence effective to increase the motility. The irradiation at an irradiance of less than 0.1 mW/cm$^2$ or more than 200 mW/cm$^2$ may not efficiently improve the sperm motility.

For these purposes, the light controller unit may be, for example, a pulse width modulation circuit.

The light controller unit may be configured to control the lighting unit to emit the light in the specified wavelengths for a predefined time period.

The predefined time period may be, for example, in a range of 1-90 min, preferably 1-60 min, more preferably 2-60 min, more preferably 5-60 min, more preferably 5-30 min, and more preferably 10-30 min.

For this purpose, the light controller unit may be, for example, a timer.

In certain specific embodiments, the light controller unit is configured to control the irradiance and the irradiation time (i.e., the fluence) of the light in the specified wavelengths emitted from the lighting unit. In the embodiments, the light controller unit may include, for example, a pulse width modulation circuit and a timer.

In more specific embodiments, the light controller unit may be configured to control the lighting unit in such a manner that the fluence of the light irradiated from the lighting unit to the sperm container is, for example, in a range of 450-7000 mJ/cm$^2$, preferably 450-6500 mJ/cm$^2$, more preferably 450-6000 mJ/cm$^2$, more preferably 500-6000 mJ/cm$^2$, more preferably 500-5500 mJ/cm$^2$, more preferably 500-5000 mJ/cm$^2$, more preferably 500-4500 mJ/cm$^2$, more preferably 550-4500 mJ/cm$^2$, more preferably 550-4000 mJ/cm$^2$, more preferably 550-3500 mJ/cm$^2$, more preferably 550-3000 mJ/cm$^2$, more preferably 600-3000 mJ/cm$^2$, more preferably 600-2500 mJ/cm$^2$, more preferably 600-2000 mJ/cm$^2$, more preferably 600-1500 mJ/cm$^2$, more preferably 650-1500 mJ/cm$^2$, more preferably 650-1000 mJ/cm$^2$. In the context of the present treatment apparatus, the "fluence" is an amount that is measured at an area on the inner or outer surface (preferably the outer surface) of the sperm container.

In the embodiments in which the lighting unit includes a light source configured to emit the light in the specified wavelengths and a light source configured to emit light in the other wavelengths, the light controller unit may be configured to control the lighting unit in such a manner that the irradiance of the light having wavelengths in a range of 390-420 nm emitted from the lighting unit is 50% or more, more preferably 60% or more, more preferably 70% or more, more preferably 80% or more, more preferably 90% or more, more preferably 95% or more of the total irradiance of light emitted from the lighting unit, and/or in such a manner that the lighting unit emits simultaneously or alternately the light in the specified wavelengths and the light in the other wavelengths. The embodiments can improve energy intensiveness, and increase sperm motility more efficiently.

The present treatment apparatus may further include a housing 36, 46 having in its inside, at least the holding or mounting unit and the lighting unit. In the embodiments, the light controller unit may be provided in or out of the housing.

The housing may have an opening in one of the surfaces, preferably on a top surface or a side surface, and more preferably on the side surface, and may further have a door for opening and closing the opening. Alternatively, the housing may include a housing body having an upward opening, and a cover for opening and closing the opening, which cover is coupled to the body.

The housing may have a cubic, rectangular or cylindrical shape. The housing may be made of, for example, metal (such as iron, stainless steel, aluminium or brass), glass or plastic (such as acrylic resin, polycarbonate resin or polyvinyl chloride resin). The inner space of the housing may be enveloped by a heat insulator.

The present treatment apparatus may further include a thermal controller unit to heat and/or maintain the sperm container at a predefined temperature. The embodiments can maintain the temperature of the spermatozoa in the container at a suitable temperature, thereby reducing the influence of temperature changes before, during and/or after the irradiation on the viability, fertilizing ability and/or motility of the spermatozoa.

The thermal controller unit may heat and/or keep the container at a temperature of 15-50° C. (particularly 35-45° C. or 15-30° C.), according to the kind of animal from which the spermatozoa used are derived.

The thermal controller unit may be composed of, for example, a heating body (such as heater or Peltier element) and/or a heat transfer medium (such as water, oil or metal), and a temperature controlling member 47 to control the temperature of the heating body and/or the heat transfer medium.

An example of the thermal controller unit is a heating table. In this case, the top surface of the heating table may compose the mounting unit. Another example of the thermal controller unit is a thermostatic chamber or room. In this case, the inner space of the housing may function as a thermostatic chamber or room. Where the thermal controller unit is a thermostatic water tank, the holding or mounting unit is arranged to hold the sperm container in water and the lighting unit may or may not be submersed in water, when the tank is filled with a predetermined amount of water.

EXAMPLES

Experiment 1

Methods

Preparation of Spermatozoa

In this experiment, straw-packed samples of bovine frozen semen were used. The frozen semen samples were thawed by submersion in water at 37° C. for 1 min. The thawed semen samples were placed in microtubes and centrifuged (3,000 rpm×5 min). Spermatozoa were collected by removing the medium.

The colleted spermatozoa were diluted in SP-TALP medium (Catalog Number: IVL03-100ML, Caisson Laboratories) and transferred into sterile disposable petri dishes.

Light Irradiation

The spermatozoa in the petri dishes without the covers were irradiated with overhead light.

The light sources used were:
"290LED" and "340LED" (NCSU234B series, NICHIA CORPORATION);
"365LED," "385LED" and "405LED" (NVSU233B series, NICHIA CORPORATION);
"430LED" (OCU-440 series, OSA Opto Light GmbH);
"450LED," "540LED" and "620LED" (NCS* 119B-V1 series, NICHIA CORPORATION);
"700LED," "765LED," "810LED" and "880LED" (Ceramic SMD 3838 series, EPIGAP Optronic GmbH); and
a halogen lamp (GEC10-P, EMINENT MAIN) equipped with a heat absorbing glass (KG3 50MM, Edmund Optics).

Figure 2:
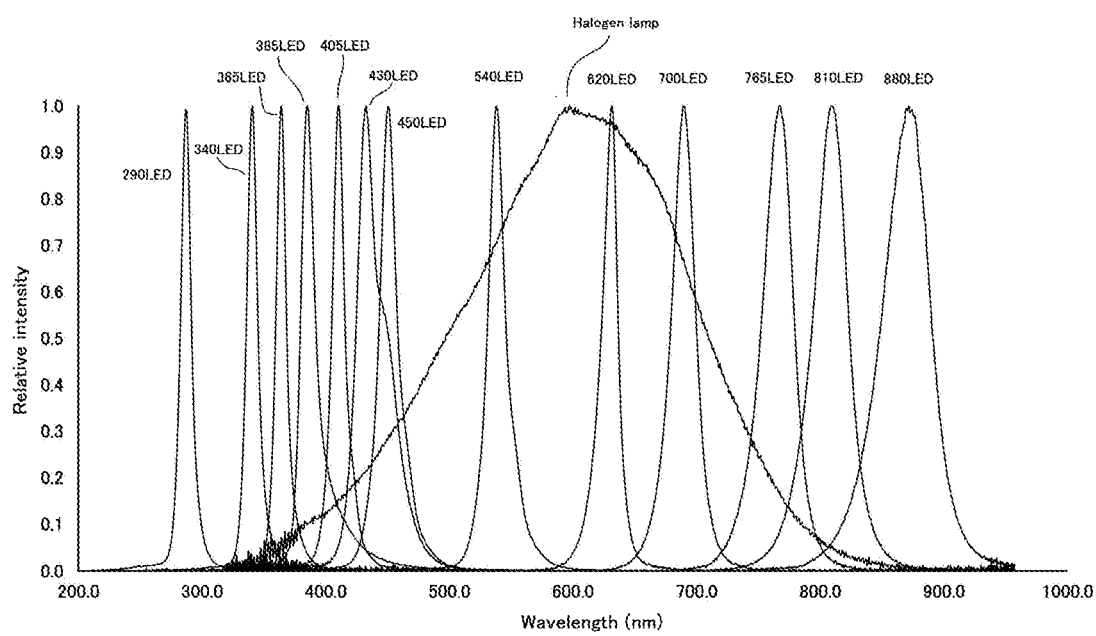
FIG. 2 illustrates the emission spectra of the light sources used in the Examples.

The emission spectra of the light sources used are given in FIG. 2.

At the top surface of the sperm suspensions, the irradiance (or fluence rate), the irradiation time and the fluence (or dose) were 0.2 mW/cm$^2$, 60 minute and 720 mJ/cm$^2$, respectively. The irradiance was measured using a combination of the Ophir Vega display and the Ophir sensor PD300-UV. A high reflecting aluminium board (MIRO series, ALANOD GmbH & Co. KG) was used to provide the whole dish with homogeneous irradiation.

Evaluation of Sperm Motility

After the irradiation under the conditions described above, an aliquot of each of the sperm suspensions was transferred into a disposable sperm counting chamber (code: sp-ace P, Kitazato Corporation) and the motility was analyzed on a sperm motility analysis system (SMAS, DITECT Co. Ltd.). The average path velocity (VAP [in μm/s]) was used to evaluate the sperm motility. Considering the variation between fields, the mean value of the measurements in three different fields was used for the evaluation.

As control, a sperm specimen was used, subjected to the same procedures as described above but not irradiated.

Results

Figure 3:
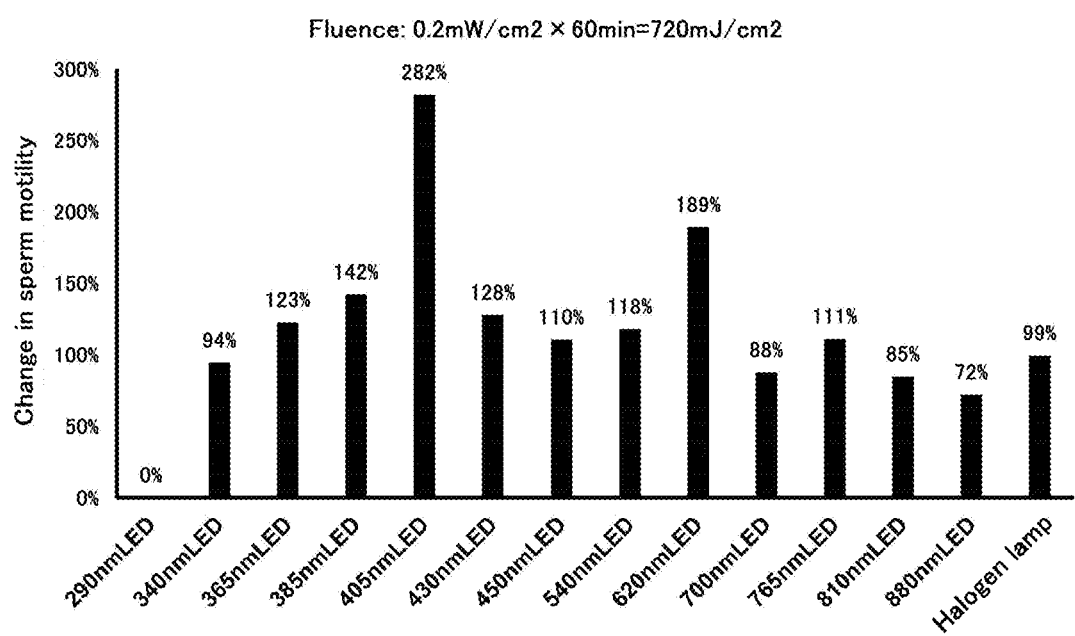
FIG. 3 shows that light irradiation in the specified wavelength range significantly increases the sperm motility.

The results are given in FIG. 3, showing the change in sperm motility by the irradiations at different wavelengths, relative to the average path velocity for the control sample (defined as 100%).

As can be seen in the figure, the irradiation of spermatozoa with light at around 405 nm significantly increased their motility. As is known in the art, the irradiation at around 620 nm also increased the motility, compared with the irradiation in the other wavelengths. However, the rate of increase was almost half of that for the irradiation at around 405 nm.

Experiment 2

Methods

This experiment was carried out as in Experiment 1 except that the irradiance was increased ten-folds (2.0 mW/cm$^2$) (fluence: 7200 mJ/cm$^2$) and the spermatozoa were not irradiated at a wavelength of 290, 340 or 365 nm (because it was concerned that the irradiation at a wavelength of 290, 340 or 365 nm at the higher irradiance, leading to increased fluence, might cause cell damage to the spermatozoa).

Results

Figure 4:
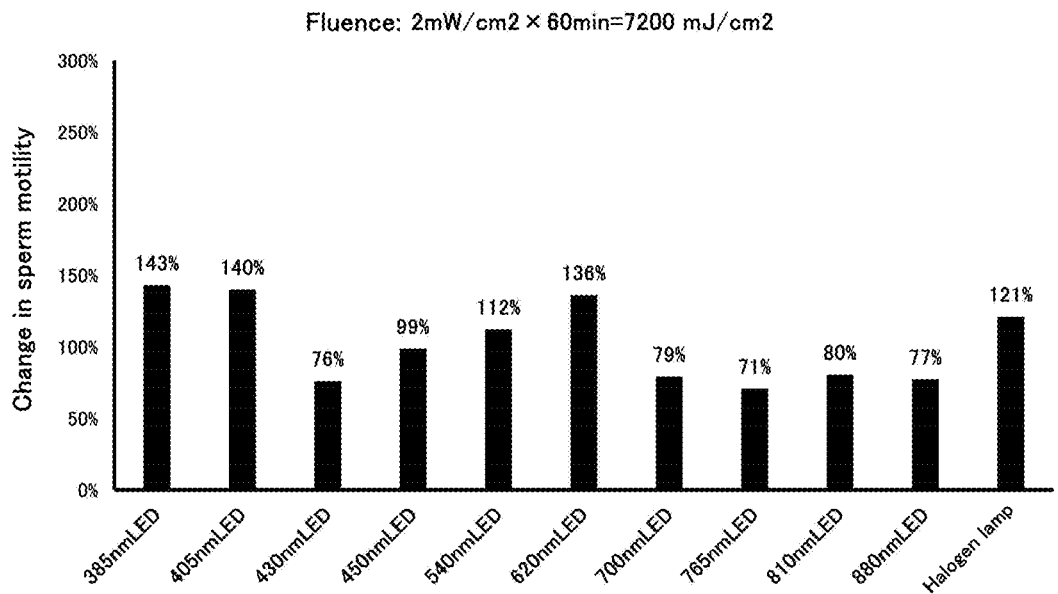
FIG. 4 shows the effect of the irradiation at a higher fluence on the sperm motility

The results are given in FIG. 4, showing the change in sperm motility by the irradiations at the higher fluence, relative to the average path velocity for the control sample (defined as 100%).

As can be seen in the figure, the irradiation of spermatozoa with light at around 405 nm still increased their motility. However, the rate of increase is almost one-fourth of that at a fluence of 720 mJ/cm$^2$. The irradiation at around 620 nm also increased the motility. However, the rate of increase is almost one-third of that at a fluence of 720 mJ/cm$^2$. The results suggest that the light irradiation at a too high fluence may reduce the increasing effect on the sperm motility.

Experiment 3

Methods

A sperm suspension prepared as in Experiment 1 was irradiated at around 405 nm at an irradiance of 0.2 mW/cm$^2$. At 15, 30, 45 and 60 minutes after the commencement of the irradiation, samples (irradiated samples) were taken from the sperm suspension.

Unirradiated samples were taken from the sperm specimen subjected to the same procedures as described above but not irradiated.

The irradiated and unirradiated samples at each time point were evaluated for sperm motility as in Experiment 1.

Results

Figure 5:
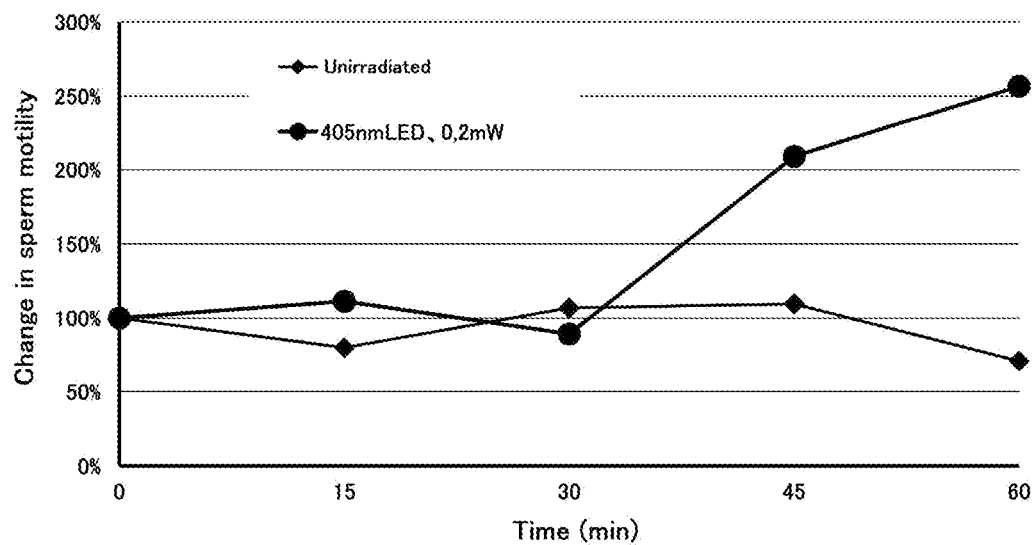
FIG. 5 shows the effect of the irradiation time on the sperm motility.

The results are given in FIG. 5, showing the relationship between the fluence of the irradiation and the sperm motility.

No increase in motility was observed in any of the unirradiated samples.

Significant increase in motility was observed in the 45-min and 60-min irradiated samples.

The results suggest that the irradiation at around 405 nm at a certain amount of fluence (at least about 300-400 mJ/cm$^2$) can increase the sperm motility.

Experiment 4

Methods

The ATP levels were measured in the 60-min irradiated sample and the corresponding unirradiated sample prepared in Experiment 3.

ATP was extracted from the samples using the AMERIC ATP kit. The extracted ATP level was quantified by luciferase assay using a luminometer (Lumat3 LB9508, Berthold Technologies).

Results

The ATP level in the irradiated sample is about 2.4 times of that in the unirradiated sample.

Without wishing to be bound by any particular theory, from the results described above and the fact that the energy source for the sperm flagellar movement is ATP produced in mitochondria, it can be reasonably deduced that the irradiation of sperm cells with the light at around 405 nm promotes mitochondrial ATP production in the cells, resulting in increasing the sperm motility. More specifically, the light at around 405 nm may activate the electron transport from hem a to hem a3-CuB in cytochrome c oxidase, which acts as a bottleneck of the electron transport chain in mitochondria.

Taken altogether, the light at around 405 nm can increase the motility of spermatozoa of any animal by the same or a similar mechanism, so long as they use ATP as the energy source for the flagellar movement.

The contents of all patents, patent applications and references cited in the present specification are incorporated by reference herein in their entireties, as if fully and specifically set forth herein, to the fullest extent permitted by applicable law.

It is to be noted that the above embodiments and examples are given by way of illustration only for the purpose of better understanding of the invention. It is to be also understood that the present invention is not limited to the particular configurations, arrangements, process steps, materials, means and devices described in the specification and the appended drawings.

Various other changes, modifications and alterations can be made to the embodiments described above without departing from the spirit and scope of the present invention. It is to be further noted that aspects of the invention described with respect to one embodiment, may be incorporated in a different embodiment although not specifically described relative thereto. That is, all embodiments and/or features of any embodiment can be combined in any way and/or combination.

REFERENCE NUMERAL LIST 10, 20, 30, 40: Apparatus according to the present disclosure
11, 21, 31, 41: Sperm container
12: Holding unit
23, 33, 43: Mounting unit
14, 24, 34, 44: Lighting unit
15, 25, 35, 45: Lighting controller unit
36, 46: Housing
47: Thermal controller unit

What is claimed is:

1. A method for treating spermatozoa of an animal, comprising:
   irradiating the spermatozoa with light having wavelengths in a range of 365-430 nm at an irradiance of 0.1 to 0.8 mW/cm$^2$.

2. The method according to claim 1, wherein the fluence is effective to increase the motility of the spermatozoa by 100% or more.

3. The method according to claim 1, wherein the fluence is effective to increase the motility of the spermatozoa by 150% or more.

4. The method according to claim 1, wherein the light having wavelengths in the range of 390-420 nm is irradiated at an irradiance of 50% or more of a total irradiance of light irradiated to the spermatozoa.

5. The method according to claim 1, wherein the light having wavelengths in the range of 390-420 nm is irradiated at an irradiance of 70% or more of a total irradiance of light irradiated to the spermatozoa.

6. The method according to claim 1, wherein the light having wavelengths in the range of 390-420 nm is a component of light having a maximum peak in a range of 390-420 nm.

7. The method according to claim 1, wherein the light having wavelengths in the range of 390-420 nm has a wavelength spectrum with a peak wavelength at 405±15 nm and a half-width of 0.1-20 nm.

8. The method according to claim 1, wherein the light having wavelengths in the range of 390-420 nm comprises light emitted by a light-emitting diode or a laser diode.

9. The method according to claim 1, wherein the light having wavelengths in the range of 390-420 nm is irradiated at an irradiance of 0.1-0.5 mW/cm$^2$.

10. The method according to claim 1, wherein the light having wavelengths in the range of 390-420 nm is irradiated for a time period of 1-90 minutes.

11. The method of claim 1, wherein the light is irradiated on the spermatozoa using a light source configured to mainly emit light having wavelengths in a range of 390-420.

12. The method of claim 1, wherein the light is irradiated on the spermatozoa using a light source configured to emit light having wavelengths in a range of 390-420.

13. The method of claim 1, wherein the fluence is in a range of 300-7000 mJ/cm$^2$.

14. The method of claim 1, wherein the fluence is at least 400 mJ/cm$^2$.

15. The method of claim 1, wherein the fluence is in a range of 400-7000 mJ/cm$^2$.

16. The method of claim 1, wherein the fluence is in a range of 450-7000 mJ/cm$^2$.

17. The method of claim 1, wherein the fluence is in a range rage of 500-7000 mJ/cm$^2$.

18. The method of claim 1, wherein the fluence is in a range of 500-6500 mJ/cm$^2$.

19. The method of claim 1, wherein the fluence is in a range rage of 500-6000 mJ/cm$^2$.

20. The method of claim 1, wherein the fluence is in a range of 500-5500 mJ/cm$^2$.

* * * * *

UNITED STATES PATENT AND TRADEMARK OFFICE
CERTIFICATE OF CORRECTION

PATENT NO. : 11,969,314 B2
APPLICATION NO. : 16/825047
DATED : April 30, 2024
INVENTOR(S) : Hirofumi Nishizono, Yasuo Fujikawa and Tomohiro Tsurumoto It is certified that error appears in the above-identified patent and that said Letters Patent is hereby corrected as shown below:

In the Claims

Claim 17, Column 16, Lines 43-44:
Please delete:
"The method of claim 1, wherein the fluence is in a range rage of 500-7000 mJ/cm$^2$."
Please replace with:
"The method of claim 1, wherein the fluence is in a range of 500-7000 mJ/cm$^2$."

Claim 19, Column 16, Lines 47-48:
Please delete:
"The method of claim 1, wherein the fluence is in a range rage of 500-7000 mJ/cm$^2$."
Please replace with:
"The method of claim 1, wherein the fluence is in a range of 500-6000 mJ/cm$^2$."

Signed and Sealed this
Third Day of September, 2024

Katherine Kelly Vidal
*Director of the United States Patent and Trademark Office*